(12) United States Patent
Looker et al.

(10) Patent No.: US 7,217,833 B2
(45) Date of Patent: May 15, 2007

(54) CARBOXYLIC ACID COMPOUNDS FOR USE AS SURFACTANTS

(75) Inventors: Brian Edgar Looker, Stevenage (GB); Christopher James Lunniss, Stevenage (GB); Alison Judith Redgrave, Stevenage (GB)

(73) Assignee: Glaxco Group Limited, Greenford (GB)

( * ) Notice: Subject to any disclaimer, the term of this patent is extended or adjusted under 35 U.S.C. 154(b) by 0 days.

(21) Appl. No.: 10/504,252

(22) PCT Filed: Feb. 12, 2003

(86) PCT No.: PCT/GB03/00547

§ 371 (c)(1),
(2), (4) Date: Feb. 24, 2005

(87) PCT Pub. No.: WO03/068722

PCT Pub. Date: Aug. 21, 2003

(65) Prior Publication Data

US 2005/0163720 A1    Jul. 28, 2005

(30) Foreign Application Priority Data

Feb. 13, 2002  (GB) ................... 0203363.7
Feb. 13, 2002  (GB) ................... 0203369.4

(51) Int. Cl.
C07C 69/66   (2006.01)
C07C 69/34   (2006.01)
A61K 37/02   (2006.01)

(52) U.S. Cl. ............... 560/180; 560/192; 514/547
(58) Field of Classification Search ........... 560/180, 560/192; 514/547; 424/45
See application file for complete search history.

(56) References Cited

U.S. PATENT DOCUMENTS

| | | | |
|---|---|---|---|
| 4,352,789 A | 10/1982 | Thiel | |
| 5,126,123 A | 6/1992 | Johnson | |
| 5,849,265 A * | 12/1998 | Li-Bovet et al. | 424/45 |
| 6,376,359 B1 | 4/2002 | Lin et al. | |
| 6,413,497 B1 | 7/2002 | Weil et al. | |
| 6,451,287 B1 | 9/2002 | Desimone et al. | |
| 2005/0048024 A1 | 3/2005 | Looker et al. | |

FOREIGN PATENT DOCUMENTS

| | | |
|---|---|---|
| EP | J0372777 A2 | 6/1990 |
| WO | WO-9104011 A1 | 4/1991 |
| WO | WO-9111173 A1 | 8/1991 |
| WO | WO-9111495 A1 | 8/1991 |
| WO | 91 14422 A | 10/1991 |
| WO | WO-9200061 A1 | 1/1992 |
| WO | WO-9200062 A1 | 1/1992 |
| WO | 96 09816 A | 4/1996 |
| WO | WO 9609816 A1 * | 4/1996 |
| WO | WO-9632099 A1 | 10/1996 |
| WO | 0224623 | 3/2002 |
| WO | 03013610 | 2/2003 |

OTHER PUBLICATIONS

Barrett et al.; "Nucleophilic substitution reactione of( alkoxymethylene)dimethylammonium chloride"; Journal of Organic Chemistry; Sep. 1998; 63(18); pp. 6273-6280;.

Leplawy et al.; "Synthesis of peptides derived from alpha-methylanaine", Tetrahedron; 1980; 11: pp. 39-51;.

Database CA 'Online! Chemical Abstracts Service, Columbus, Ohio Us; Seher. A., et al.: "Esters of 2,3-dialkoxypropionic acids and their behavior against pancreatic lipase" retrieved from STN Database accession No. 87:179724 XP002243195 see RN 64713-31-1 & Actes Congr. Mond.- Soc. Int. Etude Corps Gras, 13$^{TH}$ (1976), Vol. Symp 2, 17-26. Editor(s): Naudet, M.: Ucciani, E.: Uzzan, A. Publisher: Iterg Paris, Fr.

* cited by examiner

Primary Examiner—Samuel A Barts
Assistant Examiner—Lalitha Nagubandi
(74) Attorney, Agent, or Firm—Alice P. Bradney

(57) ABSTRACT

Compounds of formula (I)

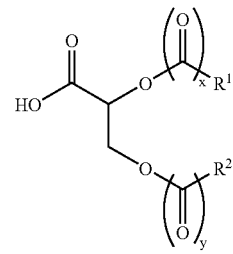

(I)

or a salt or solvate thereof, wherein:
x represents 0 or 1;
y represents 0 or 1;
$R^1$ and $R^2$ independently represent —$C_{1-9}$ alkylene$C_{1-6}$ fluoroalkyl, which fluoroalkyl moiety contains at least 1 fluorine atom and not more than 3 consecutive perfluorocarbon atoms and wherein the $R^1$ and/or $R^2$ moiety is optionally interrupted by an ether link, processes for their preparation, use of the compounds in the preparation of pharmaceutical formulations and the formulations are described.

18 Claims, No Drawings

CARBOXYLIC ACID COMPOUNDS FOR USE AS SURFACTANTS

This application if filed pursuant to 35 U.S.C. § 371 as a United States National Phase Application of International Patent Application Ser. No. PCT/GB03/00547 filed Feb. 12, 2003, which claims priority from Great Britain Application No. 0203363.7 filed in the United Kingdom on Feb. 13, 2002, and from Great Britain Application No. 0203369.4 filed in the United Kingdom on Feb. 13, 2002.

This invention relates to novel surfactants and aerosol formulations thereof for use in the administration of medicaments by inhalation.

The use of aerosols to administer medicaments has been known for several decades. Such aerosols generally comprise the medicament, one or more chlorofluorocarbon propellants and either a surfactant or a co-solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise fluorocarbons and hydrogen-containing chlorofluorocarbons, and a number of medicinal aerosol formulations using such propellant systems are disclosed in, for example, EP0372777, WO91/04011, WO91/11173, WO91/11495 and WO91/14422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvants such alcohols, alkanes, dimethyl ether, surfactants (including fluorinated and non-fluorinated surfactants, carboxylic acids, polyethoxylates etc) and even conventional chlorofluorocarbon propellants in small amounts intended to minimise potential ozone damage.

It is essential that the prescribed dose of aerosol medication delivered from the MDI to the patient consistently meets the specifications claimed by the manufacturer and comply with the requirements of the FDA and other regulatory authorities. That is, every dose delivered from the can must be the same within close tolerances. Therefore it is important that the formulation be substantially homogenous throughout the administered dose at the time of actuation of the metering valve.

In the case of suspension formulations, to control aggregation of fine particles and thereby influence the dispersability of the suspension, it is well established in the art that fluorinated surfactants may be used to stabilise micronised drug suspensions in fluorocarbon propellants such as 1,1,1,2-tetrafluoroethane (P134a) or 1,1,1,2,3,3,3-heptafluoro-n-propane (P227), see for example U.S. Pat. No. 4,352,789, U.S. Pat. No. 5,126,123, U.S. Pat. No. 5,376,359, U.S. application Ser. No. 09/580,008, WO91/11173, WO91/14422, WO92/00062 and WO96/09816.

WO92/00061 discloses non-fluorinated surfactants for use with fluorocarbon propellants.

Surprisingly, the applicants have now found that a particular group of novel low fluorine content compounds with good surfactant properties may be used to prepare novel aerosol formulations, and can be advantageous in terms of improving the stability of the aerosol formulation, reducing drug deposition, increasing shelf life and the like. In addition the compounds of the invention are adequately soluble in the fluorocarbon or hydrogen-containing chlorofluorocarbon propellants or mixtures thereof, obviating the need to use a polar adjuvant.

Thus, the invention provides a compound of formula (I)

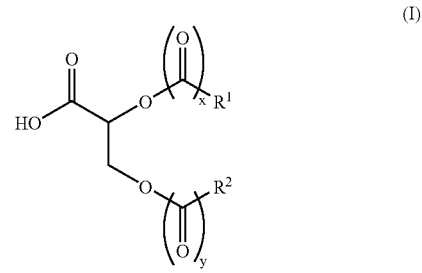

(I)

or a salt or solvate thereof, wherein:

x represents 0 or 1;

y represents 0 or 1;

$R^1$ and $R^2$ independently represent —$C_{1-9}$ alkylene$C_{1-6}$ fluoroalkyl, which fluoroalkyl moiety contains at least 1 fluorine atom and not more than 3 consecutive perfluorocarbon atoms and wherein said $R^1$ and/or $R^2$ moiety is optionally interrupted by an ether link.

Examples of $R^1$ include —$C_{1-6}$ alkylene-O—$C_{1-3}$ fluoroalkyl, such as —$(CH_2)_2$—O—$CF_3$ or —$(CH_2)_2$—O—$CF_2CF_3$ and —$C_{1-3}$ alkylene-O—$C_{1-3}$ alkylene$C_{1-3}$ fluoroalkyl such as —$(CH_2)_2$—O—$CH_2CF_3$ or —$(CH_2)_2$—O—$CH_2CF_2CF_3$.

Examples of $R^2$ include —$C_{1-6}$ alkylene-O—$C_{1-3}$ fluoroalkyl, such as —$(CH_2)_2$—O—$CF_3$ or —$(CH_2)_2$—O—$CF_2CF_3$ and —$C_{1-3}$ alkylene-O—$C_{1-3}$ alkylene$C_{1-3}$ fluoroalkyl such as —$(CH_2)_2$—O—$CH_2CF_3$ or —$(CH_2)_2$—O—$CH_2CF_2CF_3$.

In one aspect the invention provides a compound of formula (II)

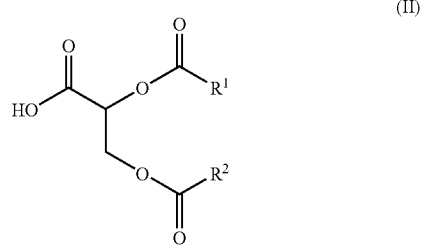

(II)

wherein $R^1$ and $R^2$ are as defined above.

In another aspect the invention provides a compound of formula (III)

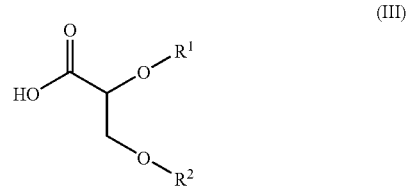

(III)

wherein $R^1$ and $R^2$ are as defined above.

In the embodiments of the invention preferably $R^1$ and $R^2$ independently represent —$C_{1-9}$alkylene$C_{1-6}$ fluoroalkyl, which fluoroalkyl moiety contains at least 1 fluorine atom and not more than 3 consecutive perfluorocarbon atoms.

More preferably $R^1$ represents —$C_{1-6}$ alkylene$C_{1-3}$ fluoroalkyl more preferably —$C_{1-3}$ alkylene$C_{1-3}$ fluoroalkyl, especially —$C_2$ alkylene$C_{1-2}$ fluoroalkyl, particularly —$CH_2CH_2CF_2CF_3$.

More preferably $R^2$ represents —$C_{1-6}$ alkylene$C_{1-3}$ fluoroalkyl more preferably —$C_{1-3}$ alkylene$C_{1-3}$ fluoroalkyl, especially —$C_2$ alkylene$C_{1-2}$ fluoroalkyl, particularly —$CH_2CH_2CF_2CF_3$.

Most preferably $R^1$ represents the same as $R^2$.

Preferably x represents 1.

Preferably y represents 1.

Preferably x represents the same as y.

Salts include alkali metal salts such as sodium and potassium and tertiary alkyl ammonium salts such as tert-butyl ammonium.

Preferably compounds of formula (I), (II) or (III) will be present as the free acid.

Compounds of formula (I), (II) or (III) contain one or more chiral centres. It will be understood that compounds of formula (I), (II) or (III) include all optical isomers of the compounds of formula (I), (II) or (III) and mixtures thereof, including racemic mixtures thereof.

In a further aspect the invention provides a pharmaceutical aerosol formulation which comprises particulate medicament, a fluorocarbon or hydrogen-containing chlorofluorocarbon propellant, or mixtures thereof, and a compound of formula (I) as described above.

The compounds of formula (I), (II) or (III) employed for the preparation of formulations according to the present invention are effective stabilisers at low concentrations relative to the amount of medicament. Thus, the amount of compound of formula (I), (II) or (III) employed is desirably in the range of 0.05% to 20% w/w, particularly 0.5% to 10% w/w, more particularly 0.5% to 5% w/w, relative to the medicament.

The particle size of the particulate (e.g. micronised) medicament should be such as to permit inhalation of substantially all of the medicament into the lungs or nasal cavity upon administration of the aerosol formulation and will thus be less than 100 microns, desirably less than 20 microns, and preferably will have a mass median aerodynamic diameter (MMAD) in the range 1–10 microns, e.g. 1–5 microns.

The final aerosol formulation desirably contains 0.005–10% w/w, preferably 0.005–5% w/w, especially 0.01–1.0% w/w, of medicament relative to the total weight of the formulation.

Medicaments which may be administered in aerosol formulations according to the invention include any drug useful in inhalation therapy and which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; anti-allergics, e.g. cromoglycate (e.g. as sodium salt), ketotifen or nedocromil (e.g. as sodium salt); antiinfectives e.g. cephalosporins, penicillins, streptomycin, sulphonamides, tetracyclines and pentamidine; anti-histamines, e.g. methapyrilene; anti-inflammatories, e.g. beclomethasone (e.g. as dipropionate), fluticasone (e.g. as propionate), flunisolide, budesonide, rofleponide, mometasone furoate, ciclesonide, triamcinolone acetonide or 6α, 9α-difluoro-11β-hydroxy-16α-methyl-3-oxo-17α-propionyloxy-androsta-1, 4-diene-17β-carbothioic acid S-(2-oxo-tetrahydro-furan-3-yl) ester; anti-tussives, e.g. noscapine; bronchodilators, e.g. albuterol (e.g. as free base or as sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol, 4-hydroxy-7-[2-[[2-[[3-(2-phenylethoxy)pro-pyl]sulfonyl]ethyl]amino]ethyl-2(3H)-benzothiazolone; diuretics, e.g. amiloride; anti-cholinergics, e.g. ipratropium (e.g. as bromide), tiotropium, atropine or oxitropium; hormones, e.g. cortisone, hydrocortisone or prednisolone; xanthines, e.g. aminophylline, choline theophyllinate, lysine theophyllinate or theophylline; therapeutic proteins and peptides, e.g. insulin or glucagon. It will be clear to a person skilled in the art that, where appropriate, the medicaments may be used in the form of salts, (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant. It will be further clear to a person skilled in the art that where appropriate, the medicaments may be used in the form of a pure isomer, for example, R-albuterol or RR-formoterol.

Particularly preferred medicaments for administration using aerosol formulations in accordance with the invention include anti-allergics, bronchodilators and anti-inflammatory steroids of use in the treatment of respiratory disorders such as asthma, COPD or rhinitis by inhalation therapy, for example cromoglycate (e.g. as sodium salt), albuterol (e.g. as free base or sulphate), salmeterol (e.g. as xinafoate), formoterol (e.g. as fumarate), terbutaline (e.g. as sulphate), reproterol (e.g. as hydrochloride), a beclomethasone ester (e.g. as diproprionate), a fluticasone ester (e.g. as propionate). Salmeterol, especially salmeterol xinafoate, albuterol sulphate, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Thus suitable combinations include bronchodilators (e.g. albuterol or isoprenaline) in combination with an anti-inflammatory steroid (e.g. beclomethasone ester); a bronchodilator in combination with an anti-allergic (e.g. cromoglycate). Exemplary combinations also include: ephedrine and theophylline; fenoterol and ipratropium; isoetharine and phenylephrine; albuterol (e.g. as free base or as sulphate) and beclomethasone ester (e.g. as dipropionate); budesonide and formoterol (e.g. as fumarate) which is of particular interest; and salmeterol (particularly as salmeterol xinafoate) and fluticasone ester (e.g. as propionate) also of particular interest.

The propellants for use in the invention may be any fluorocarbon or hydrogen-containing chlorofluorocarbon or mixtures thereof having a sufficient vapour pressure to render them effective as propellants. Preferably the propellant will be a non-solvent for the medicament. Suitable propellants include, for example, $C_{1-4}$hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds, preferably binary mixtures, with other fluorocarbons or hydrogen-containing chlorofluorocarbons, for example, $CHClF_2$, $CH_2F_2$ and $CF_3CH_3$. Particularly preferred as propellants are $C_{1-4}$ hydrogen-containing fluorocarbons such as 1,1,1,2-tetrafluoroethane ($CF_3CH_2F$) and 1,1,1,2,3,3,3-heptafluoro-n-propane ($CF_3CHFCF_3$) or mixtures thereof. Preferably a single fluorocarbon or hydrogen-containing chlorofluorocarbon is employed as the propellant e.g. 1,1,1,2-tetrafluoroethane (HFA 134a) or 1,1,1,2,3,3,3-heptafluoro-n-propane (HFA 227), especially 1,1,1,2-tetrafluoroethane.

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

If desired the propellant may additionally contain a volatile adjuvant such as a saturated hydrocarbon, for example, propane, n-butane, isobutane, pentane and isopentane or a dialkyl ether, for example, dimethyl ether. In general, up to 50% w/w of the propellant may comprise a volatile hydrocarbon, for example 1 to 30% w/w. However, formulations which are substantially free of volatile adjuvants are preferred. In certain cases, it may be desirable to include appropriate amounts of water, which can be advantageous in modifying the dielectric properties of the propellant.

Polar adjuvants which may if desired, be incorporated into the formulations according to the present invention include, for example, $C_{2-6}$ aliphatic alcohols and polyols such as ethanol, isopropanol and propylene glycol and mixtures thereof. Preferably ethanol will be employed. In general only small quantities (e.g. 0.05 to 3.0% w/w) of polar adjuvants are required and the use of quantities in excess of 5% w/w may disadvantageously tend to dissolve the medicament. Formulations preferably contain less than 1% w/w, e.g. about 0.1% w/w of polar adjuvant. Polarity may be determined, for example, by the method described in European Patent Application Publication No. 0327777.

However as the compounds of formula (I), (II) or (III) are adequately soluble in the fluorocarbon or hydrogen-containing chlorofluorocarbon propellant the need to use a polar adjuvant is obviated. This is advantageous as polar adjuvants especially ethanol are not suitable for use with all patient groups. Formulations containing a compound of formula (I), (II) or (III) which avoid use of a polar adjuvant are preferred.

In addition to one or more compounds of the general formula (I), (II) or (III) the formulations according to the present invention may optionally contain one or more further ingredients conventionally used in the art of pharmaceutical aerosol formulation. Such optional ingredients include, but are not limited to, taste masking agents, sugars, buffers, antioxidants, water and chemical stabilisers.

A particularly preferred embodiment of the invention provides a pharmaceutical aerosol formulation consisting essentially of one or more particulate medicament(s), one or more fluorocarbon or hydrogen-containing chlorofluorocarbon propellant(s) and one or more compound(s) of formula (I), (II) or (III).

A further embodiment of the invention is a sealed container capable of withstanding the pressure required to maintain the propellant as a liquid, such as a metered dose inhaler, containing therein the aerosol formulation as described above.

The term "metered dose inhaler" or MDI means a unit comprising a can, a secured cap covering the can and a formulation metering valve situated in the cap. MDI system includes a suitable channelling device. Suitable channelling devices comprise, for example, a valve actuator and a cylindrical or cone-like passage through which medicament may be delivered from the filled canister via the metering valve to the nose or mouth of a patient, for example, using a mouthpiece actuator.

As an aspect of this invention there are also provided processes for the preparation of compounds of formula (I), (II) or (III).

Therefore a process for preparing a compound of formula (I) is provided which comprises:
(a) oxidation of a compound of formula (IV)

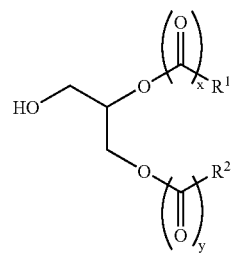

(IV)

or a salt or solvate thereof, wherein $R^1$, $R^2$, x, and y are as defined above; or
(b) deprotection of a derivative of a compound of formula (I) in which the carboxylic acid group is protected.

In process (a) methods for oxidising a primary alcohol to the corresponding carboxylic acid, using strong oxidising agents, are well known to persons skilled in the art.

Suitable reagents include chromic acid as described in Chem. Pharm. Bull. 21 (10) 2265–2267 (1973), permanganate e.g. potassium permanganate, nitric acid, acidic chromiun trioxide and 2,2,6,6-tetramethyl-1-piperidinyloxy free radical (TEMPO). Permanganate is preferred for use in process (a), especially potassium permanganate. The oxidation will generally take place in water at a non-extreme temperature, for example, 0 to 100° C. such 70° C.

In process (b) examples of carboxylic acid protecting groups and means for their removal can be found in "Protecting Groups In Organic Synthesis" by Theodora Green and Peter G. M Wuts (John Wiley and Sons Inc 1999). Suitable carboxylic acid protecting groups include but are not limited to carboxylic acid esters e.g. t-butyl esters, 2,2,2-trichloroethyl esters, aryl esters, benzyl esters including p-nitrobenzyl esters. Protecting groups may be removed by acid or base catalysed hydrolysis or by catalytic hydrogenolysis. Where the carboxylic acid is protected as a benzyl ester, the protecting group may be removed, for example, by hydrogenolysis. Where the carboxylic acid is protected as a t-butyl ester, the protecting group may be removed, for example, by hydrolysis with trifluoroacetic acid. Where the carboxylic acid is protected as a 2,2,2-trichloroethyl ester, the protecting group may be removed, for example, using zinc and acetic acid. Where appropriate protecting groups will be chosen to ensure they can be selectively removed.

A process for preparing a compound of formula (IV) or a protected derivative thereof comprises:
(c) preparing a compound of formula (IV) or a protected derivative thereof (in which $R^2$ represents the same as $R^1$) by reacting glycerol, or a derivative thereof wherein a primary hydroxyl group is protected, with a compound of formula ($V^1$)

(V¹)

wherein $R^1$ and x are as defined above and $L^1$ represents a leaving group or —OH; or (d) reacting a compound of formula (V¹)

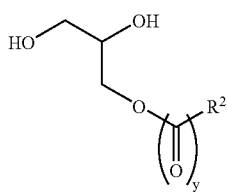
(VI¹)

or a derivative thereof wherein the primary hydroxyl is protected, wherein $R^2$ and y are as defined above, with a compound of formula (V¹) as defined above; or (e) reacting a compound of formula (V²)

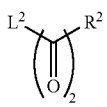
(V²)

wherein $R^2$ and y are as defined above and $L^2$ represents a leaving group or —OH with a compound of formula (VI²)

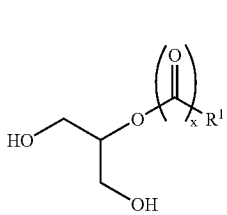
(VI²)

or a derivative thereof wherein a primary hydroxyl is protected and wherein $R^1$ and x are defined above; or (f) preparing a compound of formula (IV), or a protected derivative thereof in which $R^2$ represents the same as $R^1$, by reacting a compound of formula (VII)

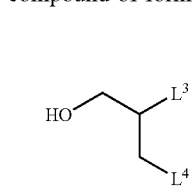
(VII)

or a derivative thereof in which the primary hydroxyl is protected, wherein $L^3$ and $L^4$ independently represent a leaving group with an acid of formula (V¹) wherein $L^1$ represents —OH, as defined above, or a salt thereof; or (g) reacting a compound of formula (VIII¹)

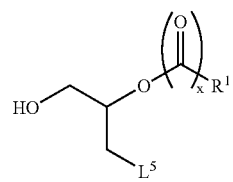
(VIII¹)

or a derivative thereof in which the primary hydroxyl is protected, wherein $R^1$ and x are as defined above and $L^5$ represents a leaving group, with an acid of formula (V²) wherein $L^2$ represents —OH, as defined above, or a salt thereof; or (h) reacting a compound of formula (VIII²)

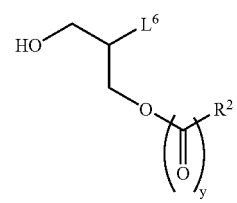
(VIII²)

or a derivative thereof in which the primary hydroxyl is protected, wherein $R^2$ and y are as defined above and $L^6$ represents a leaving group, with an acid of formula (V¹) wherein $L^1$ represents —OH, as defined above, or a salt thereof; or (i) deprotecting a protected compound of formula (IV).

In each process the non-reacting hydroxyl group(s) will preferably be protected, for example, as the benzyl or THP ether, especially wherein the non-reacting hydroxyl is a primary hydroxyl as it may be the preferred site of reaction.

Examples of protecting groups (e.g. for hydroxyl) and means for their removal can be found in "Protecting Groups In Organic Synthesis" by Theodora Green and Peter G. M Wuts (John Wiley and Sons Inc 1999). Suitable hydroxyl-protecting groups include, but are not limited to, carboxylic acid esters e.g. acetate ester, aryl esters, benzoate esters, ethers e.g. benzyl ether and p-methoxybenzyl ether, tetrahydropyranyl ether and silyl ethers e.g. tert-butyldimethylsilyl ether. Preferably hydroxyl groups are protected as the benzyl ether or the tetrahydropyranyl (THP) ether. Especially preferred is the benzyl ether.

Protecting groups can be removed by acid or base catalysed hydrolysis or catalytic hydrogenolysis. Silyl ethers may require hydrogen fluoride or tetrabutylammonium fluoride to be cleaved. Where a hydroxyl is protected as the benzyl ether, the protecting group may be removed, for example, by hydrogenolysis. Where a hydroxyl is protected as the THP ether, the protecting group may be removed, for example, by acid hydrolysis. Where appropriate protecting groups will be chosen to ensure they can be selectively removed.

In process (c) suitable leaving groups for $L^1$ include halogen, for example, chloride and anhydride, which may be prepared, for example, using the triethylamine salt of a —$C_{1-3}$ alkyl acid using methodology as described in Tetrahedron 1960, 11, 39. Preferably $L^1$ represents —OH. The process is generally performed under basic conditions, for example, in the presence of triethylamine or pyridine, in a suitable solvent, for example, dichloromethane (DCM), tetrahydrofuran (THF), dimethylformamide (DMF) or similar, at a non-extreme temperature, for example, 0 to 50° C. such as room temperature. Where compounds of formula ($V^1$) are carboxylic acids i.e. where $L^1$ represents —OH a coupling agent, for example, hydroxybenzotriazole (HOBT), dicyclohexylcarbodiimide (DCC) or o-(7-azabenzotriazol-1-yl)-N,N,N',N'-tetramethyluronium hexafluorophosphate (HATU) together with diisopropylethylamine (DIPEA) may also be present. An alternative process which may provide stereocontrol is described *J Org Chem,* 1998, 63, 6273.

When $R^1$ represents the same as $R^2$ usually at least two molar equivalents of compound of formula ($V^1$) will be used in this process. Preferably a excess of compound of formula ($V^1$) will be used.

In processes (d) and (e), conditions analogous to those employed in process (c) are suitable. Suitable leaving groups for $L^2$, include those described above for $L^1$.

In process (e the reaction will generally take place in the presence of a base, for example triethylamine or 1,8-diazabicyclo[5,4,0]undec-7-ene (DBU), in a suitable inert solvent, for example, dichloromethane (DCM), dimethylformamide (DMF) or acetonitrile at non-extreme temperatures, for example, −10 to 80° C. such as room temperature.

Suitable leaving groups for $L^3$ and $L^4$ include halogen, for example chloride or bromide, —O-tosyl, —O-mesyl or —O-triflyl.

In processes (g) and (h) conditions analogous to those employed in process (f) are suitable. Suitable leaving groups for $L^5$ and $L^6$ include those defined above for $L^3$.

Preferably non-reacting hydroxyl group(s) will be protected e.g. as a benzyl or a THP ether. Where there is more than one non-reacting hydroxyl group preferably each non-reacting hydroxyl will be protected by different protecting groups to facilitate selective removal e.g. tetrahydropyranyl (THP) ether and benzyl ether. It is especially advantageous that when the non-reacting hydroxyl is a primary alcohol it is protected as it may react preferentially to the desired site of reaction.

However variations of these reactions where the leaving group and the reacting hydroxyl are swapped may also be contemplated. Leaving groups will be used as necessary in these reactions.

Compounds of formula ($VI^1$), or a protected derivative thereof may be prepared by a process which comprises reacting a compound of formula ($V^2$) with a selectively protected derivative of glycerol wherein the unreacting hydroxyl groups are protected.

The reaction can be performed under conditions analogous to those described above for process (c) described above.

Alternatively compounds of formula ($VI^1$) may be prepared by a process which comprises:
(j) reacting epibromohydrin or epichlorohydrin with a compound of formula ($V^2$) wherein $L^2$ represents —OH, as defined above, or a salt thereof; and
(k) reacting the product of step (j) with water.

Epoxides can be cleaved under acidic or basic conditions. The product of the reaction can be controlled by choice of the nucleophile and reaction conditions. The advantage of using an epihalohydrin is that the three carbons in the starting material may be differentiated.

Usually reaction (j) will be performed in a suitable solvent, for example, tetrahydrofuran (THF) at a non-extreme temperature, for example, −10 to 50° C. such as 0° C. to room temperature.

Compounds of formula ($VI^2$) may be prepared using analogous methods to those described above for the preparation of compounds of formula ($VI^1$).

Compounds of formula (V) can be prepared from glycerol by converting the desired hydroxyls into leaving groups using known methods. Reagents for converting hydroxyl groups into good leaving groups include halogenating agents such as carbon tetrabromide and triphenylphosphine, thionyl chloride or phosphorus pentachloride or may be effected by treatment with methane sulphonyl chloride or p-toluene sulphonic chloride. Protecting groups will be used as necessary in these reactions.

Compounds of formula ($VIII^1$) may be prepared from compounds of formula ($VI^2$), preferably a protected derivative thereof, using, for example, a halogenating agent to convert the desired hydroxyl in the latter compound into a good leaving group.

Compounds of formula ($VIII^2$) may be prepared from compounds of formula ($VI^1$) by analogous methods.

Compounds of formula ($V^1$) and ($V^2$) are either known or may be prepared by known methods, for example, acids can be prepared by oxidation of the corresponding alcohol and acid halides can be prepared by reacting the corresponding acid with a halogenating agent such as thionyl chloride.

Variations of the above methods which are common in the art are within the scope of this invention.

Alternatively compounds of formula (I) may be prepared by a process which comprises: (L) reacting a protected derivative of glycidic acid, for example wherein the carboxylic acid moiety is protected as the benzyl ester or p-nitrobenzyl ester, with an acid of formula ($V^2$) wherein $L^2$ represents —OH, as defined above, or a salt thereof to give a compound of formula (IX)

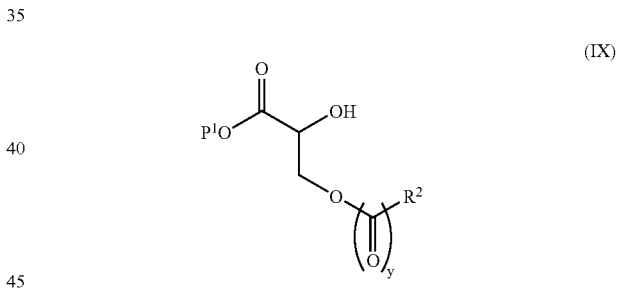

(IX)

wherein $R^2$ and y are as defined above and $P^1$ represents a protecting group;
(m) reacting the product of step (L) with an acid of formula ($III^1$) wherein $L^1$ represents —OH or a salt thereof; and
(n) followed, if necessary, by deprotection.

Process (L) may be performed using one molar equivalent of an acid of formula ($V^2$) which may be in the presence of a catalytic amount of, for example, sulphuric acid, toluene sulphonic acid or a Lewis acid such as $BF_3$ etherate, $FeCl_3$ or $ZnCl_2$ optionally in the presence of an appropriate solvent, for example DCM, DMF or THF, at a non-extreme temperature, for example, 0 to 100° C. such as room temperature for between 1 and 24 hours.

Process (m) may be performed under standard conditions in the presence of a coupling agent as described above in process (c). Alternatively process (m) may be performed under conditions as described for process (L) above however the reaction will usually be performed at a non-extreme temperature elevated temperature, for example 25 to 100° C. such as 50 to 70° C., for between 1 and 24 hours. Wherein the $R^1$ represents the same as $R^2$ processes (L) and (m) may be combined to give a "one step" reaction wherein at least two molar equivalents of an acid of formula ($V^1$) are reacted at a non-extreme elevated temperature under analogous conditions to those described above for process (L).

The deprotection in process (n) may be performed using hydrogenolysis.

Compounds of formula (VIII) are either known or may be prepared by known methods.

Compounds of formula (IV), ($VI^1$), ($VI^2$), ($VIII^1$), ($VIII^2$) and (IX) are new and form an aspect of the invention.

In addition processes for preparing formulations including one or more compounds of formula (I) form an aspect of this invention.

The formulations of the invention may be prepared by dispersal of the medicament and a compound of formula (I) in the selected propellant in an appropriate container, e.g. with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The suspension stability of the aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaela 1988, pages A204–207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

MDI canisters generally comprise a container capable of withstanding the vapour pressure of the propellant used such as a plastic or plastic-coated glass bottle or preferably a metal can, for example an aluminium or an alloy thereof which may optionally be anodised, lacquer-coated and/or plastic-coated (e.g. incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g., see Byron, above and WO96/32099). Preferably the canister is fitted with a cap assembly, wherein a formulation metering valve is situated in the cap, and said cap is crimped in place.

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

A further aspect of this invention comprises a process for filling the said formulation into MDIs.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquefied propellant is pressure filled through the charge vessel into a manufacturing vessel, together with liquefied propellant containing the surfactant. The drug suspension is mixed before recirculation to a filling machine and an aliquot of the drug suspension is then filled through the metering valve into the canister.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler system for administration of the medicament into the lungs or nasal cavity of a patient. Metered dose inhalers are designed to deliver a fixed unit dosage of medicament per actuation or "puff", for example, in the range of 10 to 5000 micrograms of medicament per puff.

Administration of medicament may be indicated for the treatment of mild, moderate, severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example, from 1 to 8 times per day, giving for example 1, 2, 3 or 4 puffs each time.

Suitable daily doses, may be, for example, in the range 50 to 200 micrograms of salmeterol, 100 to 1000 micrograms of albuterol, 50 to 2000 micrograms of fluticasone propionate or 100 to 2000 micrograms of beclomethasone dipropionate, depending on the severity of the disease.

Thus, for example, each valve actuation may deliver 25 microgram salmeterol, 100 microgram albuterol, 25, 50, 125 or 250 microgram fluficasone propionate or 50, 100, 200 or 250 microgram beclomethasone dipropionate. Doses for Seretide™, which is a combination of salmeterol and fluticasone propionate, will usually be those given for the corresponding individual component drugs. Typically each filled canister for use in a metered dose inhaler system contains 60, 100, 120, 160 or 240 metered doses or puffs of medicament.

An appropriate dosing regime for other medicaments will be know or readily available to persons skilled in the art.

The use of the compounds of formula (I), (II) or (III) or mixtures thereof as described above as a surfactant, especially in the preparation of a pharmaceutical formulation; use of a formulation as described above in inhalation therapy e.g. for the treatment or prophylaxis of disease, particularly respiratory disorders; and use of a metered dose inhaler system in the treatment or prophylaxis of respiratory disorders are all alternative aspects of this invention.

A still further aspect of the present invention comprises a method of treating respiratory disorders such as, for example, asthma and/or COPD which comprises administration by inhalation of an effective amount of a formulation as herein described.

The following non-limiting examples serve to illustrate the invention.

EXAMPLES

LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0–0.7 min 0% B, 0.7–4.2 min 100% B, 4.2–5.3 min 0% B, 5.3–5.5 min 0% B at a flow rate of 3 ml/min. The mass spectra were recorded on a flow injection Hewlett Packard engine using thermospray positive ion mode or a Micromass series II mass spectrometer using electrospray positive and negative mode (ES+ve and ES–ve).

Example 1

2,3-Bis[(4,4,5,5,5-pentafluoronentanoyl)oxy]propanoic acid (a) 4.4,5,5,5-Pentafluoropentanoic acid The title compound was synthesised by the method described in Organic Process Research and Development 1999, 3, 363–364.

(b) 2-[(4,4,5,5,5-Pentafluoropentanoyl)oxy]-1-{[(phenylmethyl)oxy]methyl}ethyl 4,4,5,5,5-pentafluoropentanoate The product of step (a) (118 g) and carbonyl duimidazole (98.8 g) were dissolved in tetrahydrofuran (1900 mL) and stirred at 50° C. for 1 hour. A solution of D/L benzyl glycerol (50.0 g) and 1,8-diazabicyclo[5.4.0]undec-7-ene (92.7 g) in tetrahydrofuran (230 mL) was added over ten minutes and the reaction stirred at 50° C. for 2 hours, before being allowed to cool to 20° C. The reaction mixture was partitioned between methyl tert-butyl ether (2.36 L) and 1M hydrochloric acid (2.36 L). The aqueous layer was discarded and the organic layer washed sequentially with water (2.36 L) and saturated sodium bicarbonate solution (2.0 L). The organic phase was distilled out and diluted with methyl tert-butyl ether (2.56 L). This was washed with brine (2.56 L), water (2.56 L), dried over magnesium sulphate and the solvent removed in vacuo. Purification of the residue by column chromatography on silica gel (Biotage) eluting with 10:1 cyclohexane:ethyl acetate gave the title compound (110 g) as an orange/yellow oil.

Mass spectrum m/z 548 [$MNH_4^+$]

(c) 2-Hydroxy-1-{[(4.4,5,5,5-pentafluoropentanoyl)oxy]methyl}ethyl-4.4,5,5,5-pentafluoropentanoate The product of step (b) (110 g) was dissolved in tetrahydrofuran (1100 mL) and 10% Pd/C (11 g) was added. The reaction was placed under an atmosphere of hydrogen and stirred at 20° C. for 15 hours. The reaction mixture was filtered through a bed of celite and the solvent was removed in vacuo to give the title compound (97.6 g) as a light yellow oil.

Mass spectrum m/z 458 [$MNH_4^+$]

(d) 2,3-Bis[(4.4.5,5,5-pentafluoronentanoyl)oxy]propanoic acid

The product of step (c) (300 mg) and tetraethylammonium hydrogen sulphate (1.5 mg) were dissolved in water (3 mL) and heated with stirring to 70° C. To this solution was added dropwise a solution of sodium permanganate (152 mg) in water (2 mL). Once the addition was complete the reaction was stirred at 70° C. for 4 hours and then at 20° C. for 17 hours. The reaction mixture was filtered through a pad of Celite. The resulting solution was partitioned between dichloromethane (150 mL) and water (150 mL). The aqueous layer was acidified to pH 1 by the addition of 2M hydrochloric acid and then extracted with dichloromethane (3×150 mL). The combined organic layers were dried over magnesium sulphate and the solvent removed in vacuo. Purification by Isolute $NH_2$ SPE cartridge, eluting with 2M ammonia in methanol gave the title compound as a clear oil (24 mg).

Mass spectrum m/z 453 [$M^-$] LC Retention time 3.59 mins

Experimental Data

Salmeterol xinafoate formulations in HFA 134a, of strength 25 µg per actuation, and 10% w/w (relative to drug) of the relevant surfactant compound of formula (I) were prepared in crimped glass bottles using salmeterol xinafoate (8.7 mg), HFA 134a (18 g) and the relevant compound (0.87 mg). The control was prepared without the addition of a surfactant.

Particle Size

Table 1 shows mean particle size data determined by image analysis using a Galai CIS-100 particle size analyser for sample formulations prepared as described above. In this measurement, particle size is represented as the equivalent diameter of a circle of equal area to the object. The mean is the average of 4 determinations. The particle size measurement was obtained by transferring the suspensions to a pressurised cell, and video-imaging the sample under shear via a microscope objective.

The equivalent diameter is defined as the diameter of a circle of equal area to the object.

$$\text{Equivalent Diameter} = \sqrt{\frac{\text{Area}}{\pi}}$$

The mean equivalent diameter can be weighted by number, length or volume. e.g. For three particles with equivalent diameters of x, y and z:

$$\text{Mean Number weighted diameter} = \left(\frac{1}{3}\right)x + \left(\frac{1}{3}\right)y + \left(\frac{1}{3}\right)z$$

$$\text{Mean Length weighted diameter} = \left(\frac{x}{x+y+z}\right)x + \left(\frac{y}{x+y+z}\right)y + \left(\frac{z}{x+y+z}\right)z$$

The data shows that the surfactant compound of Example 1 has suspension stabilising properties, thereby discouraging flocculation of drug particles. This is seen by the reduction in average particle size ("mean length weighted diameter") when the said compound is incorporated into the formulation. Furthermore, the standard deviation and the relative standard deviation for the formulations incorporating the compound of Example 1 are advantageously reduced.

TABLE 1

Particle Size Data

| | Mean Length weighted diameter μm | Standard Deviation μm | Relative Standard Deviation |
|---|---|---|---|
| Control | 29.3 | 1.7 | 5.7 |
| Example 1 | 21.5 | 1.1 | 5.3 |

Andersen Cascade Impaction Data

The formulation, the preparation of which is described above, was profiled using an Andersen Cascade Impactor. Ten actuations at "beginning of use" (BoU) were collected in the impactor from an inhaler after 4 priming actuations were fired to waste. The drug delivered was then quantified by HPLC analysis. Testing was performed at the initial timepoint (following sample preparation). The results, in Table 2 are shown as the mean analysis of 3 cans/inhalers.

The profile obtained was used to determine total dose emitted dose (ex-valve and ex-actuator) and the fine particle mass (FPM, defined as the sum of stages 3–5). The percentage fine particle mass expresses the FPM as a percentage of the total dose emitted (ex-valve). The FPM is used as a measure of the proportion of the drug likely to reach the therapeutic target in the lungs.

The data shows, that in the presence of the surfactant compound of Example 1, there is an increase in both the absolute doses emitted and the absolute FPM. There is also a significant increase in the percentage FPM.

TABLE 2

Total Ex-Valve & Ex-actuator Emitted Dose and FPM Data Using Cascade Impaction

| | Timepoint | Total Dose Emitted (Ex-Valve) μg | Total Dose Emitted (Ex-Actuator) μg | FPM μg | % FPM |
|---|---|---|---|---|---|
| Control | Initial | 23.3 | 20.3 | 9.9 | 42.6 |
| Example 1 | Initial | 23.9 | 21.1 | 12.0 | 50.3 |

Content Uniformity

The content uniformity of the formulation, the preparation of which is described above, was assessed by dose through use testing. Testing was performed on 10 cans/inhalers at "beginning of use" (BoU) and "end of use" (EoU). After each inhaler had been primed (4 shots fired to waste), actuations 1 and 2 (BoU) were collected. The next 116 actuations of each inhaler were then fired to waste using an automated method and actuations 119 and 120 (EoU) collected.

Assessment of content uniformity was performed at the initial timepoint (following sample preparation). Mean results from the two BoU actuations (1+2 for 10 inhalers) and the two EoU actuations (119+120 for same 10 inhalers) together with the percentage relative standard deviation (% RSD) for the 10 cans are shown in Table 3. The data shows, that in the presence of the surfactant compound of Example 1, there is in increase in the emitted BoU dose and a reduction in the EoU % RSD. The presence of the surfactant therefore improves the content uniformity of the inhaler. Furthermore the formulations containing the compound of Example 1, advantageously, show a reduction in the relative standard deviation at the BoU and EoU.

TABLE 3

| | Control | | Example 1 | |
|---|---|---|---|---|
| Timepoint | BoU dose μg | EoU dose μg | BoU dose μg | EoU dose μg |
| Initial | 20.1 (2.6% RSD) | 24.8 (5.6% RSD) | 21.2 (1.7% RSD) | 25.1 (3.5% RSD) |

The invention claimed is:

1. A compound of formula (I)

or a salt or solvate thereof, wherein:

x represents 0 or 1;

y represents 0 or 1;

$R^1$ and $R^2$ independently represent —$C_{1-9}$alkylene$C_{1-6}$fluoroalkyl, which fluoroalkyl moiety contains at least 1 fluorine atom and not more than 3 consecutive perfluorocarbon atoms and wherein said $R^1$ and/or $R^2$ moiety is optionally interrupted by an ether link.

2. A compound according to claim 1, wherein $R^1$ is —$C_{1-6}$alkylene$C_{1-3}$fluoroalkyl.

3. A compound according to claim 2, wherein $R^2$ is —$C_{1-6}$alkylene$C_{1-3}$fluoroalkyl.

4. A compound according to claim 1, wherein x represents 1.

5. A compound according to claim 1, wherein y represents 1.

6. A compound according claim 1, which is 2,3-Bis[(4,4,5,5,5-pentafluoropentanoyl)oxy]propanoic acid.

7. A pharmaceutical aerosol formulation which comprises particulate medicament, a fluorocarbon or hydrogen-containing chlorofluorocarbon propellant, or mixtures thereof, and a compound of formula (I) according to claim 1.

8. A pharmaceutical formulation according to claim 7, wherein the amount of compound of formula (I) is in the range 0.5% to 5% w/w, relative to the medicament.

9. A metered dose inhaler containing a formulation according to claim 7.

10. A process for the preparation of compounds of formula (I) comprising (a) oxidation of a compound of formula (IV)

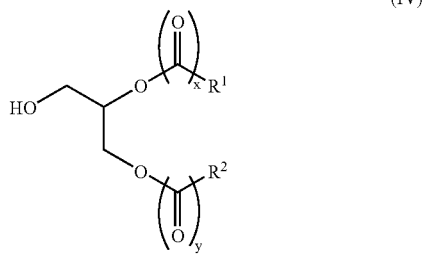

(IV)

or a salt or solvate thereof, wherein:

x represents 0 or 1;

y represents 0 or 1;

$R^1$ and $R^2$ independently represent —$C_{1-9}$ alkylene$C_{1-6}$ fluoroalkyl, which fluoroalkyl moiety contains at least 1 fluorine atom and not more than 3 consecutive perfluorocarbon atoms and wherein said $R^1$ and/or $R^2$ moiety is optionally interrupted by an ether link; or (b) deprotection of a derivative of a compound of formula (I) in which the carboxylic acid group is protected.

11. A compound according to claim 1, wherein $R^1$ is —$C_{1-3}$alkylene$C_{1-3}$fluoroalkyl.

12. A compound according to claim 1, wherein $R^1$ is —$C_2$alkylene$C_{1-2}$fluoroalkyl.

13. A compound according to claim 1, wherein $R^1$ is —$CH_2CH_2CF_2CF_3$.

14. A compound according to claim 11, wherein $R^2$ is —$C_{1-3}$alkylene$C_{1-3}$fluoroalkyl.

15. A compound according to claim 11, wherein $R^2$ is —$C_2$alkylene$C_{1-2}$fluoroalkyl.

16. A compound according to claim 11, wherein $R^2$ is —$CH_2CH_2CF_2CF_3$.

17. A compound according to claim 1, wherein x is 1 and y is 1.

18. A method of treating a respiratory disorder in a subject in need thereof comprising administering by inhalation an effective amount of a formulation according to claim 7 to the subject.

* * * * *

UNITED STATES PATENT AND TRADEMARK OFFICE
CERTIFICATE OF CORRECTION

PATENT NO.       : 7,217,833 B2                                             Page 1 of 1
APPLICATION NO.  : 10/504252
DATED            : May 15, 2007
INVENTOR(S)      : Brian Edgar Looker, Christopher James Lunniss and Alison Redgrave It is certified that error appears in the above-identified patent and that said Letters Patent is hereby corrected as shown below:

On title page
Item (56) References Cited
U.S. PATENT DOCUMENTS should include:

-- 5,376,359   12/1994   Johnson --

Corrections to OTHER PUBLICATIONS: Item [56]

Barrett et al. should read
-- Barrett et al.; "Nucleophilic substitution reactions of (alkoxymethylene) dimethylammonium chloride"; Journal of Organic Chemistry; Sep.1998; 63(18); pp. 6723-6280; --

"Leplawy et al." should read
-- Leplawy et al,; "Synthesis of peptides derived from alphamethylalanine", Tetrahedron; 1960; 11: pp. 39-51; --

Database CA should read
-- Database CA 'Online! Chemical Abstracts Service, Columbus, Ohio US; Seher. A., et al.: "Esters of 2,3-dialkoxypropionic acids, and their behavior against pancreatic lipase" retrieved from STN Database accession No. 87:179724 XP002243195 see RN 64713-31-1 & Actes Congr. Mond.-Soc. Int. Etude Corps Gras, 13TH (1976), Vol. Symp 2, 17-26. Editor(s): Naudet, M.: Ucciani, E.: Uzzan, A, Publisher: Iterg Paris, Fr, --

Signed and Sealed this

Thirteenth Day of November, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,217,833 B2 | Page 1 of 1 |
| APPLICATION NO. | : 10/504252 | |
| DATED | : May 15, 2007 | |
| INVENTOR(S) | : Brian Edgar Looker, Christopher James Lunniss and Alison Redgrave | |

It is certified that error appears in the above-identified patent and that said Letters Patent is hereby corrected as shown below:

On the title page
Item (56) References Cited

U.S. PATENT DOCUMENTS should include:

--5,376,359    12/1994    Johnson --

Corrections to OTHER PUBLICATIONS:
Item [56]
Barrett et al. should read
      -- Barrett at al.; "Nucleophilic substitution reactions of (alkoxymethylene) dimethylammonium chloride"; Journal of Organic Chemistry; Sep. 1998; 63(18); pp. 6723-6280;--

Leplawy et al. should read
      -- Leplawy et al.; "Synthesis of peptides derived from alphamethylalanine, Tetrahedron; 1960; 11: pp. 39-51; --

Database CA should read
      -- Database CA 'Online! Chemical Abstracts Service, Columbus, Ohio US; Seher. A., et al.: "Esters of 2,3-dialkoxypropionic acids and their behavior against pancreatic lipase" retrieved from STN Database accession No.87:179724 XP002243195 see RN 64713-31-1 & Actes Congr. Mond.-Soc. Int. Etude Corps Gras, 13TH (1976), Vol. Symp 2, 17-26. Editor(s): Naudet, M.: Ucciani, E.: Uzzan, A. Publisher: Iterg Paris, Fr. --

Signed and Sealed this

Fourth Day of December, 2007

JON W. DUDAS
*Director of the United States Patent and Trademark Office*